US012734067B2

(12) United States Patent
Karri et al.

(10) Patent No.: US 12,734,067 B2
(45) Date of Patent: Sep. 15, 2026

(54) EYE HEALTH DATA ANALYSIS USING ARTIFICIAL INTELLIGENCE

(71) Applicant: International Business Machines Corporation, Armonk, NY (US)

(72) Inventors: Venkata Vara Prasad Karri, Visakhapatnam (IN); Sarbajit K. Rakshit, Kolkata (IN)

(73) Assignee: International Business Machines Corporation, Armonk, NY (US)

(*) Notice: Subject to any disclaimer, the term of this patent is extended or adjusted under 35 U.S.C. 154(b) by 1412 days.

(21) Appl. No.: 17/301,376

(22) Filed: Mar. 31, 2021

(65) Prior Publication Data

US 2022/0313485 A1 Oct. 6, 2022

(51) Int. Cl.
*A61F 9/00* (2006.01)
*A61B 3/10* (2006.01)
(Continued)

(52) U.S. Cl.
CPC ........... *A61F 9/0017* (2013.01); *A61B 3/101* (2013.01); *A61B 5/4836* (2013.01);
(Continued)

(58) Field of Classification Search
CPC ..... A61F 9/0017; A61B 3/101; A61B 5/4836; A61B 5/6821; A61B 2560/0252;
(Continued)

(56) References Cited

U.S. PATENT DOCUMENTS 8,385,998 B2 2/2013 Zhang
2018/0152627 A1* 5/2018 Bostick ................. G06V 40/18
(Continued)

FOREIGN PATENT DOCUMENTS

CA 2948010 A1 10/2015

OTHER PUBLICATIONS

Wang et al. "Explore technology innovation and intelligence for IoT (Internet of Things) based eyewear technology", Technological Forecasting and Social Change, vol. 127, 2018, pp. 281-290, ISSN 0040-1625, https://doi.org/10.1016/j.techfore.2017.10.001. (Year: 2018).*

(Continued)

*Primary Examiner* — Karlheinz R. Skowronek
(74) *Attorney, Agent, or Firm* — Jordan T. Schiller

(57) ABSTRACT

Eye health data analysis using artificial intelligence includes receiving, by a mobile device, biometric data from one or more sensors located on a contact lens substrate on a user's eye. The biometric data includes, at least in part, a moisture level of the user's eye. The mobile device identifies a plurality of environmental parameters associated with the user's location using surrounding internet-of-things devices that are communicatively connected with the contact lens substrate and the mobile device. In response to determining that the moisture level in the user's eye is below a predetermined threshold, the mobile device generates a recommendation including automatically adjusting at least one of the plurality of environmental parameters and displays the generated recommendation to the user using an augmented reality system in the contact lens substrate.

15 Claims, 6 Drawing Sheets

(51) Int. Cl.
*A61B 5/00* (2006.01)
*G06N 20/00* (2019.01)
*G16H 40/67* (2018.01)
*G16H 50/30* (2018.01)

(52) U.S. Cl.
CPC ........... *A61B 5/6821* (2013.01); *G06N 20/00* (2019.01); *G16H 40/67* (2018.01); *G16H 50/30* (2018.01); *A61B 2560/0252* (2013.01); *A61B 2562/029* (2013.01)

(58) Field of Classification Search
CPC A61B 2562/029; A61B 5/1103; G06N 20/00; G16H 40/67; G16H 50/30; G16H 40/63
See application file for complete search history.

(56) References Cited

U.S. PATENT DOCUMENTS

| | | | | |
|---|---|---|---|---|
| 2018/0335647 | A1* | 11/2018 | Béduer ................ | A61K 9/0048 |
| 2019/0260870 | A1* | 8/2019 | Spivack .................. | G06F 3/011 |
| 2021/0007670 | A1* | 1/2021 | Lamrani .............. | A61B 5/6847 |

OTHER PUBLICATIONS

Aydndoan et al., “Applications of augmented reality in ophthalmology [Invited],” Biomed. Opt. Express 12, 511-538 (Jan. 2021) (Year: 2021).*

Wang et al. “Explore technology innovation and intelligence for IoT (Internet of Things) based eyewear technology”, Technological Forecasting and Social Change, vol. 127, 2018, pp. 281-290, ISSN 0040-1625, https://doi.org/10.1016/j.techfore 2017.10.001 (Year: 2017).*

Aydndoan et al., “Applications of augmented reality in ophthalmology [Invited],” Biomed. Opt. Express 12, 511-538 (2021) (Year: 2021).*

Kim et al. “Recent advances in smart contact lenses.” Advanced Materials Technologies 5.1 (2020): 1900728 (Year: 2020).*

Maulvi et al. “Design and optimization of a novel implantation technology in contact lenses for the treatment of dry eye syndrome: In vitro and in vivo evaluation.” Acta biomaterialia 53 (2017): 211-221 (Year: 2017).*

“Dry eyes”, Mayo Clinic, Sep. 24, 2020, 10 pages, <https://www.mayoclinic.org/diseases-conditions/dry-eyes/symptoms-causes/syc-20371863>.

Dias, et al., “Wearable Health Devices-Vital Sign Monitoring, Systems and Technologies”, Sensors 2018, 18, 2414, 28 pages, <https://www.ncbi.nlm.nih.gov/pmc/articles/PMC6111409/>.

Galan, Nicole, “Contact lenses for dry eye: Options, lifestyle changes, and causes”, Medical News Today, Feb. 19, 2017, 6 pages, <https://www.medicalnewstoday.com/articles/315885>.

Kusama, et al., “Self-Moisturizing Smart Contact Lens Employing Electroosmosis”, Advanced Materials Technologies, Nov. 28, 2019, 1900889, 9 pages, <https://www.researchgate.net/publication/337600206_Self-Moisturizing_Smart_Contact_Lens_Employing_Electroosmosis>.

Markoulli, et al., “Contact lens wear and dry eyes: challenges and solutions”, Clinical Optometry, vol. 9, Feb. 1, 20175, pp. 41-48, <https://www.ncbi.nlm.nih.gov/pmc/articles/PMC6095561/>.

Mell, et al., “The NIST Definition of Cloud Computing”, National Institute of Standards and Technology, Special Publication 800-145, Sep. 2011, 7 pages.

Mukamal, Reena, “High-Tech Contact Lenses That Go Beyond Correcting Vision”, American Academy of Ophthalmology, Feb. 5, 2020, 6 pages, <https://www.aao.org/eye-health/tips-prevention/smart-contact-lens-tech-beyond-vision-correction>.

Raghu, “Office AC can make eyes dry, itchy and red: Here’s what you need to do”, The Economic Times, Last Updated: Apr. 3, 2018, 3 pages, <https://economictimes.indiatimes.com/magazines/panache/office-ac-can-make-eyes-dry-itchy-and-red-heres-what-you-need-to-do/articleshow/63589695.cms>.

Smythe, Jennifer L., “New contact lens materials, solutions expand options for dry eye patients”, Healio, Primary Care Optometry News, Issue: Nov. 2003, 9 pages, <https://www.healio.com/news/optometry/20120225/new-contact-lens-materials-solutions-expand-options-for-dry-eye-patients>.

* cited by examiner

EYE HEALTH DATA ANALYSIS USING ARTIFICIAL INTELLIGENCE

BACKGROUND

The present invention generally relates to the field of artificial intelligence (AI), and more particularly to analyzing data received from smart contact lenses.

Different environmental factors such as pollutants, humidity, temperature variations, etc., can affect various parts of the eye (e.g., cornea, conjunctiva, etc.) leading to eye disorders including conjunctivitis, dry eye, and the like. The eyes are the most vulnerable organs to atmospheric and environmental changes. Although the eyes are naturally structured to protect themselves from foreign objects (e.g., dust, wind, bright light, etc.), for the purpose of vision they need to remain open. Prolonged exposure to adverse environmental conditions can have serious consequences on eye health and even cause vision impairment.

SUMMARY

The present disclosure recognizes the shortcomings and problems associated with managing environmental conditions that can negatively impact eye health. Particularly, the need for an automated method and system to analyse eye health data that can provide real-time feedback to users based on which preventive measures can be taken to potentially avoid or reduce the incidence of eye disease. Therefore, there is a need for a method and system for analyzing data received from smart contact lenses that can facilitate the management and prevention of eye disorders.

Shortcomings of the prior art are overcome and additional advantages are provided through the provision of a computer-implemented method for analyzing data received from smart contact lenses. The method includes receiving, by a mobile device, biometric data from one or more sensors located on a contact lens substrate on a user's eye, the biometric data including, at least in part, a moisture level of the user's eye, identifying, by the mobile device, a plurality of environmental parameters associated with the user's location using surrounding internet-of-things (IoT) devices, the contact lens substrate being communicatively connected with the IoT devices and the mobile device, in response to determining that the moisture level in the user's eye is below a predetermined threshold, the mobile device generates a recommendation including automatically adjusting at least one of the plurality of environmental parameters and displays the generated recommendation to the user using an augmented reality system in the contact lens substrate.

Another embodiment of the present disclosure provides a computer program product for analyzing data received from smart contact lenses, based on the method described above.

Another embodiment of the present disclosure provides a computer system for analyzing data received from smart contact lenses, based on the method described above.

BRIEF DESCRIPTION OF THE DRAWINGS

The following detailed description, given by way of example and not intended to limit the invention solely thereto, will best be appreciated in conjunction with the accompanying drawings, in which.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Figure 1:
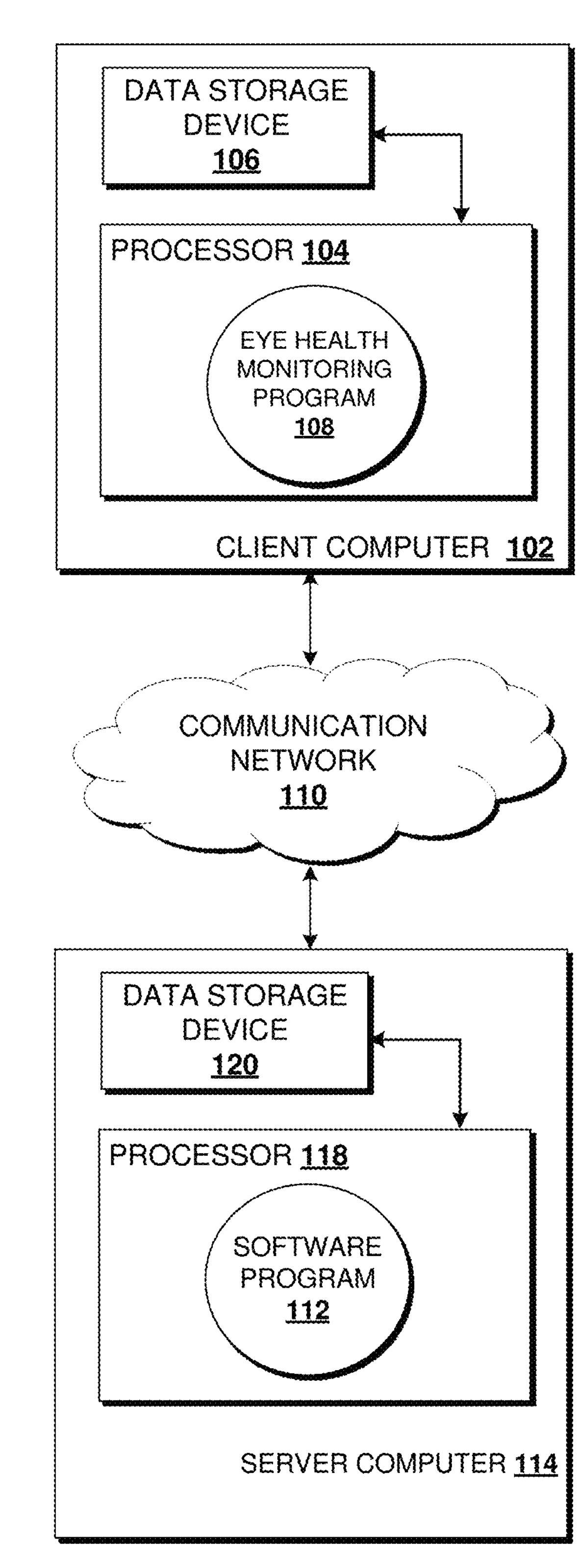
FIG. 1 is a block diagram illustrating a networked computer environment, according to an embodiment of the present disclosure.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

Surrounding environmental conditions can have an impact on eye health. A common eye disorder caused or worsen by adverse environmental conditions is dry eye syndrome. Dry eye disease is a common condition that occurs when tears aren't able to provide adequate lubrication for the eyes. Tears can be inadequate and unstable for many reasons. For example, dry eyes may occur when not enough tears or poor-quality tears are produced. This tear instability leads to inflammation and damage of the eye's surface. A lack of moisture in the air in heated or air-conditioned indoor spaces can make eyes read, itchy and irritated. Additionally, the time spent looking at computer screens, cell phones, etc., without breaks can also contribute to this condition. Adverse environmental conditions can also be found outdoors, for example, smoke, dust, winds, and extreme hot or cold temperatures can make the eyes feel dry. Other factors causing dry eye disease can include allergies, medications, certain medical conditions, hormones, and age. Frequently, many people experiencing dry eyes can find relief simply by changing their environment.

Recent advances in wearable electronics combined with wireless communications are essential to the realization of medical applications through health monitoring technologies. Specifically, smart contact lenses, which are capable of monitoring the physiological information of the eye and tear fluid, can provide real-time, noninvasive medical diagnostics. Embodiments of the present disclosure take advantage of existing smart contact lens and wireless technologies to provide real-time feedback to smart contact lens wearers regarding surrounding environmental factors that can negatively impact eye health. Particularly, environmental conditions that can cause or worsen dry eye disease.

Therefore, embodiments of the present invention provide a method, system, and computer program product for analyzing data received from smart contact lenses. The following described exemplary embodiments provide a system, method, and computer program product to, among other things, provide users with a real-time feedback regarding surrounding environmental factors that can cause dry eye symptoms using an augmented reality system. Specifically, embodiments of the present disclosure may allow a user to adjust different environmental parameters such as humidity, temperature, etc., based on real-time feedback from a plurality of internet-of-things (IoT) devices communicatively connected to the smart lenses and user's mobile device.

Thus, the present embodiments have the capacity to improve the technical field of artificial intelligence by obtaining information regarding a user's current eye condition, associating the obtained information with different environmental parameters corresponding to a location of the user, creating a knowledge base of environmental factors affecting the user's eye condition, and automatically generating and displaying an action plan to the user using an augmented reality system. Additionally, using tear storage chambers located in a perimeter of the smart contact lenses, the proposed embodiments can activate a tear release mechanism in response to detecting dry eye conditions.

Referring now to FIG. 1, an exemplary networked computer environment 100 is depicted, according to an embodiment of the present disclosure. FIG. 1 provides only an illustration of one embodiment and does not imply any limitations with regard to the environments in which different embodiments may be implemented. Many modifications to the depicted environment may be made by those skilled in the art without departing from the scope of the invention, as recited by the claims.

The networked computer environment 100 may include a client computer 102 and a communication network 110. The client computer 102 may include a processor 104, that is enabled to run an eye health monitoring program 108, and a data storage device 106. Client computer 102 may be, for example, a mobile device, a telephone (including smartphones), a personal digital assistant, a netbook, a laptop computer, a tablet computer, a desktop computer, or any type of computing devices capable of accessing a network.

The networked computer environment 100 may also include a server computer 114 with a processor 118, that is enabled to run a software program 112, and a data storage device 120. In some embodiments, server computer 114 may be a resource management server, a web server or any other electronic device capable of receiving and sending data. In another embodiment, server computer 114 may represent a server computing system utilizing multiple computers as a server system, such as in a cloud computing environment.

The eye health monitoring program 108 running on client computer 102 may communicate with the software program 112 running on server computer 114 via the communication network 110. As will be discussed with reference to FIG. 4, client computer 102 and server computer 114 may include internal components and external components.

The networked computer environment 100 may include a plurality of client computers 102 and server computers 114, only one of which is shown. The communication network 110 may include various types of communication networks, such as a local area network (LAN), a wide area network (WAN), such as the Internet, the public switched telephone network (PSTN), a cellular or mobile data network (e.g., wireless Internet provided by a third or fourth generation of mobile phone mobile communication), a private branch exchange (PBX), any combination thereof, or any combination of connections and protocols that will support communications between client computer 102 and server computer 114, in accordance with embodiments of the present disclosure. The communication network 110 may include wired, wireless or fiber optic connections. As known by those skilled in the art, the networked computer environment 100 may include additional computing devices, servers or other devices not shown.

Plural instances may be provided for components, operations, or structures described herein as a single instance. Boundaries between various components, operations, and data stores are somewhat arbitrary, and particular operations are illustrated in the context of specific illustrative configurations. Other allocations of functionality are envisioned and may fall within the scope of the present invention. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the present invention.

Figure 2:
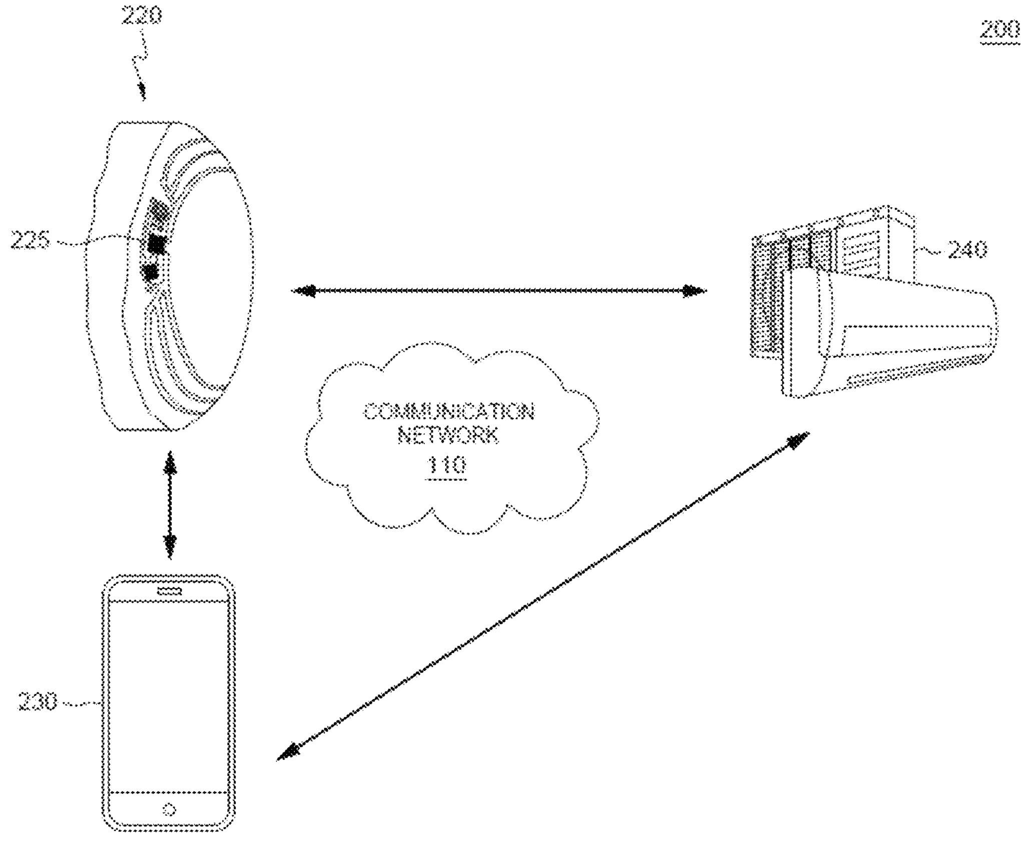
FIG. 2 depicts a computer system for analyzing data received from smart contact lenses, according to an embodiment of the present disclosure.

Referring now to FIG. 2, an exemplary diagram depicting a computer system 200 for analyzing data received from smart contact lenses is shown, according to an embodiment of the present disclosure. In this embodiment, the computer system 200 includes a smart contact lens device 220 (hereinafter "smart contact lens") communicatively connected to one or more devices 240 and a mobile device 230 via the communication network 110.

The smart contact lens 220 includes a thin, curved contact substrate placed on a film of tears covering a surface of a user's eye. Preferably, the smart contact lens 220 is equipped with a plurality of sensors (not shown) that provide noninvasive methods to continuously detect various biomarkers and record biometric data. Specifically, the plurality of sensors in the smart contact lens 220 can include, for example, a moisture sensor (not shown) capable of detecting an amount of tear fluid in the eye (i.e., a moisture level) and a blinking pattern of the user from which a tear evaporation rate can be derived at different times. As mentioned above, some environmental conditions, such as wind and dry climates, can decrease tear volume due to increased tear evaporation. When the normal amount of tear production decreases or tears evaporate too quickly from the eyes, symptoms of dry eye can develop. In this embodiment, the plurality of sensors fitted on the smart contact lens 220 can provide noninvasive monitoring of user's tear fluid.

Further, the smart contact lens 220 is equipped with a tear storage chamber 225. The tear storage chamber 225 includes a microscopic compartment for collecting tear fluid that can be located, for example, on a perimeter of the smart contact lens 220. For illustration purposes only, without intent of limitation, only one tear storage chamber 225 is shown in the smart contact lens 220, it may be understood that the smart contact lens 220 may include more than one tear storage chamber 225. In other embodiments, the tear storage chamber 225 can be positioned in areas of the smart contact lens 220 different than the perimeter of the smart contact lens 220.

According to an embodiment, the tear storage chamber 225 allows user's tear fluid to be collected in the smart contact lens 220 during normal secretion and blinking. Specifically, the tear fluid can be automatically collected in the tear storage chamber 225 using an osmosis mechanism. As will be described in detail below, the same mechanism can be used to release the collected tear fluid in response to detecting a decrease in the amount of moisture in the user's eye.

The smart contact lens 220 may also be equipped with an augmented reality (AR) system (not shown). As known by those skilled in the art, through the use of augmented reality, the smart contact lens 220 can display information directly on a retina of the user (i.e., the wearer) of the smart contact lens 220 regardless of the focal length change of the user's eyeball. Specifically, using augmented reality, the computer system 200 can display real-time information to the user in an unobtrusive and hands-free way.

With continued reference to FIG. 2, the smart contact lens 220 can continuously communicate with the one or more devices 240 and the (paired) mobile device 230. According to an embodiment, the one or more devices 240 may include a plurality of wireless-enabled devices such as internet-of-things (IoT) devices that are capable of detecting and controlling different environmental parameters associated with a current location of the user. For example, the detected environmental parameters may include a room temperature, a humidity level, and a light intensity in the user's current location. These environmental parameters can be controlled and/or automatically adjusted by smart devices (i.e., the one or more devices 240) available in the user's location such as, for example, a smart thermostat, a smart hygrometer, and a smart light bulb.

In some embodiments, the user wearing the smart contact lens 220 may be located, for example, in a smart home where the surrounding environmental parameters can be automatically updated based on a record of user's preferences. Preferably, the one or more devices 240 existing in the user's location can collect and store information regarding the environmental parameters surrounding the user (e.g., room temperature, humidity level, light intensity) over a period of time. Stated differently, the one or more devices 240 are capable of storing and collecting historical data associated with the user's location.

It should be noted that any user data collection (e.g., environmental data, biometric data, etc.) is done with user consent via an opt-in and opt-out feature. As known by those skilled in the art, an opt-in and opt-out feature generally relates to methods by which the user can modify a participating status (i.e., accept or reject the data collection). In some embodiments, the opt-in and opt-out feature can include a software application(s) available in the mobile device or client computer 102. Additionally, the user can choose to stop having his/her information being collected or used. In some embodiments, the user can be notified each time data is being collected. The collected data is envisioned to be secured and not shared with anyone without user's consent. The user can stop the data collection at any time.

According to an embodiment, the computer system 200 can detect environmental conditions in the surroundings from the one or more devices 240 and a current condition of the user's eyes from the smart contact lens 220, based on this information the eye health monitoring program 108 (FIG. 1) in the paired mobile device 230 can determine changes in user's eye conditions and whether those changes can be the result of current environmental conditions. For example, the system 200 via the eye health monitoring program 108 (FIG. 1) may determine that the tear evaporation rate has increased (i.e., tear volume or moisture level within the eye has decreased) causing dry eye symptoms. Simultaneously, the eye health monitoring program 108 (FIG. 1) in the mobile device 230 determines that the humidity level in the room is 20%. Accordingly, the eye health monitoring program 108 (FIG. 1) in the mobile device 230 analyzes this information and generates a recommendation including an action plan for the user. The mobile device 230, via the augmented reality system in the smart contact lens 225, displays the generated recommendation to the user. The display recommendation may include, for example, instructions for increasing the humidity level in the room to at least 50%, and close eyes for at least 60 seconds.

In some embodiments, based on a history of settings of the one or more devices 240 and user's eye conditions, the computer system 200 may automatically adjust the settings of the one or more devices 240 (e.g., temperature, air flow direction, moisture level, etc.) to prevent dry eye symptoms.

In some embodiments, based on the detected moisture content in user's eyes and the surrounding environmental conditions, the computer system 200 can communicate with existing display devices (e.g., computer screen) to automatically align the display content and recommend screen display attributes and/or application level preferences specific to the user to potentially reduce eye strain while performing activities on the display device (computer screens set too high may force user's eyes to open wider). Specifically, in an exemplary embodiment, by setting the position of the display device below eye level, eye strain can be reduced which can help slowing down the tear evaporation rate between eye blinks, in addition to making work more comfortable for the user.

In such embodiments, the mobile device 230 can use the augmented reality system to guide the user during the process of adjusting the position of the display device. In embodiments in which the display device is a mobile device or tablet, the system 200 using the augmented reality capabilities of the smart contact lens 220 can show the user how to hold the device appropriately to reduce eye strain. Accordingly, the augmented reality system available in the smart contact lens 220 allows the mobile device 230 to communicate with the user in real-time to provide specific guidelines and recommendations derived from data collected from the smart contact lens 220 and the one or more device 240 that can help improving user's eye health, among other health conditions. For example, the computer system 200 may prompt the user to take a break from the computer screen, blink a few times, or close the eyes for a determined period of time.

According to an embodiment, the smart contact lens 220 collects and stores historical data associated with user's eye conditions including dry eye symptoms and a record of environmental parameters associated with user's most common locations. This historically collected data can be correlated to different situations including various environment settings to identify a pattern of eye health conditions including dry eye symptoms. Stated differently, a knowledge base of eye health conditions and environmental factors associated with the user can be generated based on data historically collected by the computer system 200 to identify situations in which dry eye symptoms can be initiated or aggravated. Accordingly, the computer system 200 can provide real-time feedback to the user via the augmented reality system or mobile device 230 to avoid such situations and thereby the dry eye symptoms.

Using the historically collected data, the computer system 200 can identify and record a baseline of environmental parameters that promote proper eye moisture levels. In some embodiments, the computer system 200 via the mobile device 230 can, per user's request, progressively adjust a setting of the one or more devices 240 to modify environmental parameters in a current location of the user based on such baseline to prevent dry eye conditions. Additional actions taken by the computer system 200 may include automatically adjusting a level of lightning in a room, a brightness of a computer screen, air flow, etc. In embodiments in which some of devices surrounding the user cannot communicate with the mobile device 230 (i.e., they are not smart devices) to be automatically adjusted, the computer system 200 via the mobile device 230 can generate and display a recommendation to the user including the optimal settings such that they user can perform the recommended adjustments manually.

It should be noted that to provide temporary relief to dry eye symptoms, the mobile device 230 can activate the release of the tear fluid collected in the tear fluid storage chamber 225.

In some embodiments, the computer system 200 can continuously analyze the eye health patterns of the user over a period of time and based on the analysis provide feedback to the user including scheduling a doctor appointment. The feedback can be provided via the mobile device 230 or the augmented reality system in the smart contact lens 220. The computer system 200 may also provide recommendations in the form of videos, or audio files related to habits for improving eye health.

In embodiments in which, two or more users are sharing a space, the system 200 can update environmental parameters based on a shared library of environmental parameters. However, the system 200 generates and displays eye health recommendations individually via the smart contact lens 220 or the mobile device 230.

Figure 3:
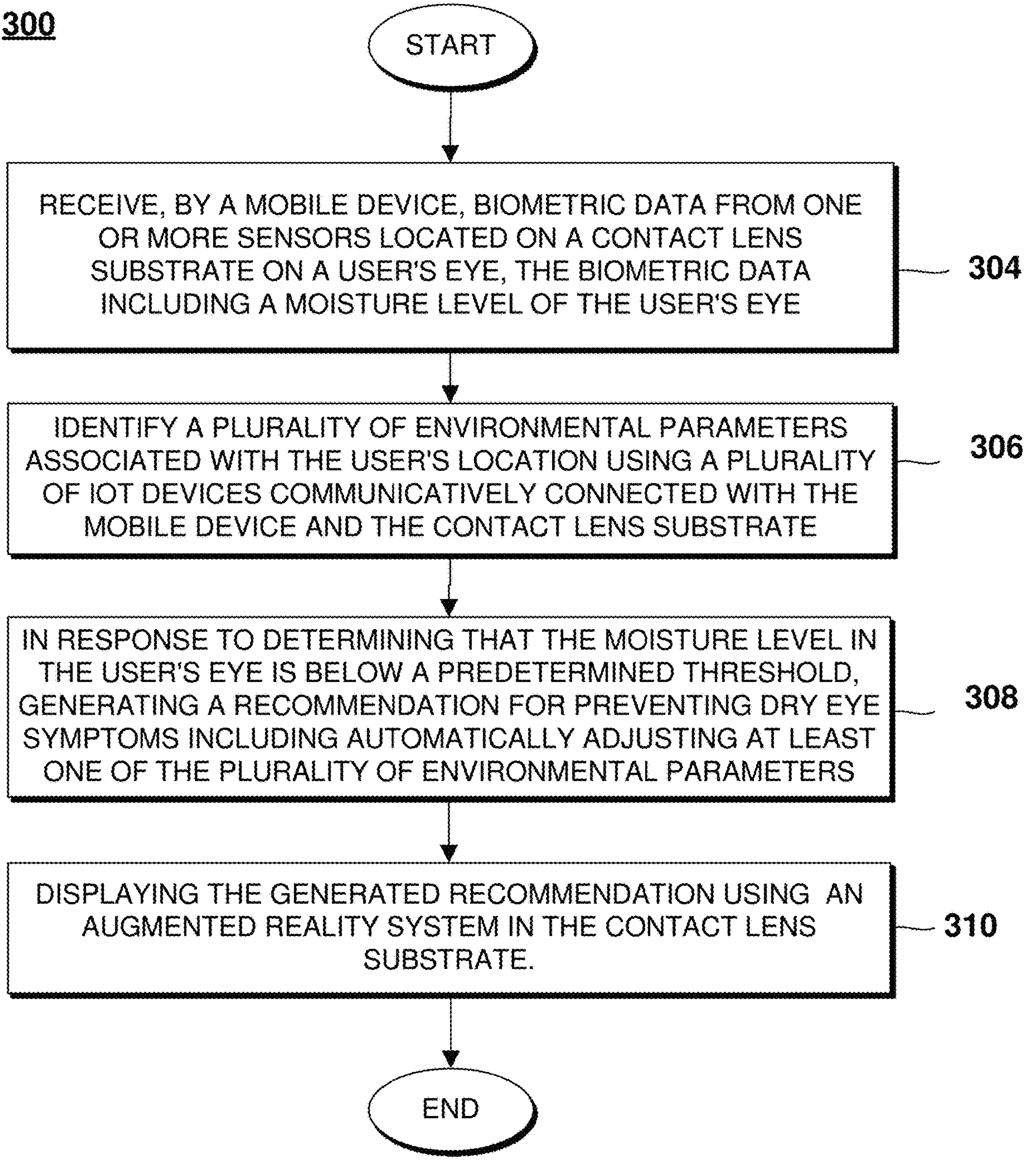
FIG. 3 depicts a flowchart illustrating the steps of a computer-implemented method for analyzing data received from smart contact lenses, according to an embodiment of the present disclosure.

Referring now to FIG. 3, a flowchart illustrating the steps of a computer-implemented method for analyzing data received from smart contact lenses is shown, according to an embodiment of the present disclosure.

The method starts at step 304 in which a mobile device, such as the mobile device 230 in FIG. 2, receives biometric data from one or more sensors located on a contact lens substrate wore by a user (e.g., the smart contact lens 220 in FIG. 2). As previously explained, the one or more sensors can collect and provide information regarding a moisture level of the user's eye to the mobile device. Additionally, the one or more sensors can collect and provide information regarding at least one of a position of the contact lens substrate within the user's eye, a movement pattern, a blinking pattern, and a tear evaporation rate based on which the mobile device can monitor eye health conditions.

At step 306, the mobile device via a plurality of IoT devices, such as the one or more devices 240 in FIG. 2, identifies a plurality of environmental parameters associated with the user's location. The contact lens substrate is communicatively connected with the plurality of IoT devices and the mobile device via a communication network, such as the communication network 110 (FIGS. 1-2). Example of environmental parameters that can associated with the user's location include a room temperature, a humidity level, a light intensity in the user's current location, and air flow direction, etc. Additional environmental parameters may include an orientation angle or position of a display device, a screen brightness, a time spent performing activities in front of the display device, a way of holding the display device, and the like.

In response to determining that the moisture level in the user's eye is below a predetermined threshold, the mobile device, at step 308, generates a recommendation including automatically adjusting at least one of the plurality of environmental parameters. The predetermined threshold for eye moisture level may be selected based on a tear evaporation rate (free blinking) of the user, which can also be determined by the one or more sensors in the contact lens substrate. For example, the predetermined threshold can be selected based on a tear evaporation rate of normal subjects. As mentioned above, an increased tear evaporation rate decreases tear volume and hence a moisture level within the eye, which in turn may cause symptoms of dry eye.

In an embodiment, the contact lens substrate further includes a tear fluid storage chamber in which tear fluid can be collected via an osmosis mechanism during normal secretion and blinking. Then, in response to determining that the eye moisture level has decreased or it is below the predetermined threshold, the mobile device can activate a mechanism for releasing the collected tear fluid from the tear fluid storage chamber to temporarily relieve dry eye symptoms.

Finally, at step 310, the mobile device displays the generated recommendation to the user using an augmented reality system in the contact lens substrate.

In additional embodiments, in response to determining that the eye moisture level is below the predetermined threshold, the mobile device can display a guide for the user to adjust in real-time at least one of an orientation angle of a screen display, a way of holding the screen display, and an eye level using the augmented reality system.

In yet another embodiment, in response to determining that the moisture level in the user's eye is within the range associated with normal tear evaporation (i.e., moisture level is normal), the proposed computer system 200 (FIG. 2) may scan the location of the user to detect current values of the environmental parameter and settings of the plurality of IoT devices. These settings associated with normal moisture level in the eyes can be recorded and reproduced at a later time, per user's request, to prevent dry eye symptoms. In some instances, the proposed method may create a library of (optimal) environmental conditions including a collection of settings of the plurality of IoT devices associated with the user experiencing a normal tear volume or moisture level. The library may be available for future use by the user. For example, in a day the user is experiencing dry eye symptoms, the user can access the library and decide to reproduce the recorded optimal environmental parameters.

The collection of data associated with the environmental parameters prior and after the user achieves dry eye relief, allows for the creation of the library of optimal environmental conditions. Then, per user's request, the library can be accessed by the system 200 (FIG. 2) to reproduce the settings of the plurality of IoT devices associated with normal moisture level. For example, the user requests a home assistant "help me relieve dry eye symptoms" on a Friday night, the system 200 (FIG. 2) looks at the environmental parameters from the library of optimal environmental conditions with the labels "night", "Friday", "night week day", "night season", after finding the corresponding settings, the system 200 (FIG. 2) starts changing the current environment setting. In some embodiments, numerous iterations can be performed on some environmental parameters depending on the user not experiencing relief from the dry eye symptoms. After experiencing relief, the computer system 200 (FIG. 2) focuses on maintaining the environmental conditions promoting a normal eye moisture level.

Therefore, embodiments of the present disclosure provide a method, system and computer program product to, among other things, monitor a user's eye health using smart contact lens and IoT technologies and provide real-time feedback regarding surrounding environmental factors that can cause dry eye symptoms using an augmented reality system. Based on the real-time feedback surrounding environmental parameters can be adjusted to provide relief to the user's symptoms.

Figure 4:
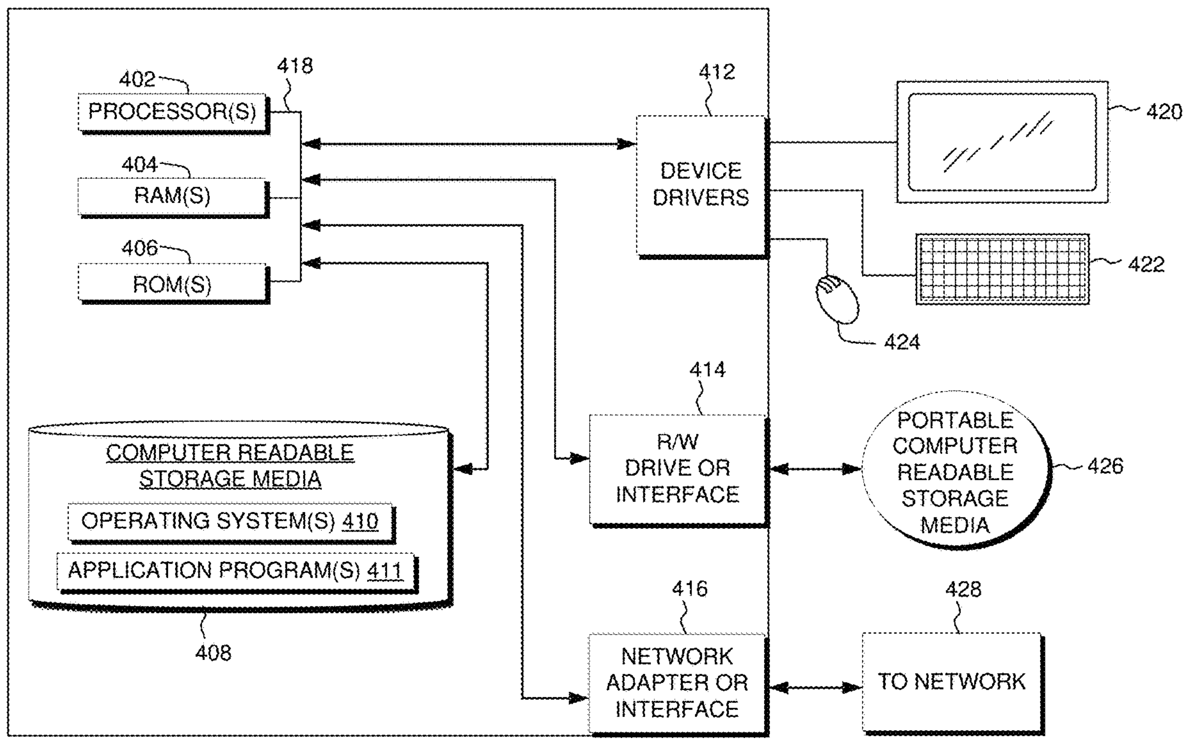
FIG. 4 is a block diagram of internal and external components of a computer system, according to an embodiment of the present disclosure.

Referring now to FIG. 4, a block diagram of components of client computer 102 and server computer 114 of networked computer environment 100 of FIG. 1 is shown, according to an embodiment of the present disclosure. It should be appreciated that FIG. 4 provides only an illustration of one implementation and does not imply any limitations regarding the environments in which different embodiments may be implemented. Many modifications to the depicted environment may be made.

Client computer 102 and server computer 114 may include one or more processors 402, one or more computer-readable RAMs 404, one or more computer-readable ROMs 406, one or more computer readable storage media 408, device drivers 412, read/write drive or interface 414, network adapter or interface 416, all interconnected over a communications fabric 418. Communications fabric 418 may be implemented with any architecture designed for passing data and/or control information between processors (such as microprocessors, communications and network processors, etc.), system memory, peripheral devices, and any other hardware components within a system.

One or more operating systems 410, and one or more application programs 411 are stored on one or more of the computer readable storage media 408 for execution by one or more of the processors 402 via one or more of the respective RAMs 404 (which typically include cache memory). In the illustrated embodiment, each of the computer readable storage media 408 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Client computer 102 and server computer 114 may also include a R/W drive or interface 414 to read from and write to one or more portable computer readable storage media 426. Application programs 411 on client computer 102 and server computer 114 may be stored on one or more of the portable computer readable storage media 426, read via the respective R/W drive or interface 414 and loaded into the respective computer readable storage media 408.

Client computer 102 and server computer 114 may also include a network adapter or interface 416, such as a TCP/IP adapter card or wireless communication adapter (such as a 4G wireless communication adapter using OFDMA technology) for connection to a network 428. Application programs 411 on client computer 102 and server computer 114 may be downloaded to the computing device from an external computer or external storage device via a network (for example, the Internet, a local area network or other wide area network or wireless network) and network adapter or interface 416. From the network adapter or interface 416, the programs may be loaded onto computer readable storage media 408. The network may comprise copper wires, optical fibers, wireless transmission, routers, firewalls, switches, gateway computers and/or edge servers.

Client computer 102 and server computer 114 may also include a display screen 420, a keyboard or keypad 422, and a computer mouse or touchpad 424. Device drivers 412 interface to display screen 420 for imaging, to keyboard or keypad 422, to computer mouse or touchpad 424, and/or to display screen 420 for pressure sensing of alphanumeric character entry and user selections. The device drivers 412, R/W drive or interface 414 and network adapter or interface 416 may include hardware and software (stored on computer readable storage media 408 and/or ROM 406).

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
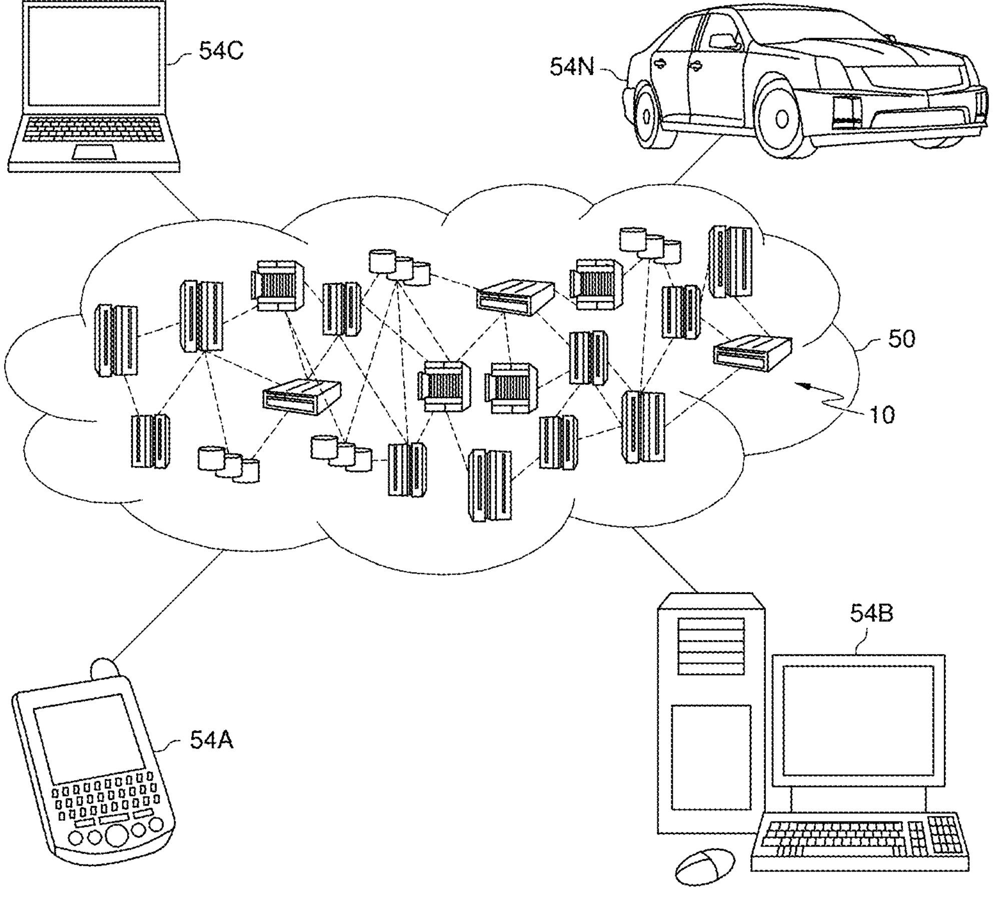
FIG. 5 is a block diagram of an illustrative cloud computing environment, according to an embodiment of the present disclosure.

Referring now to FIG. 5, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
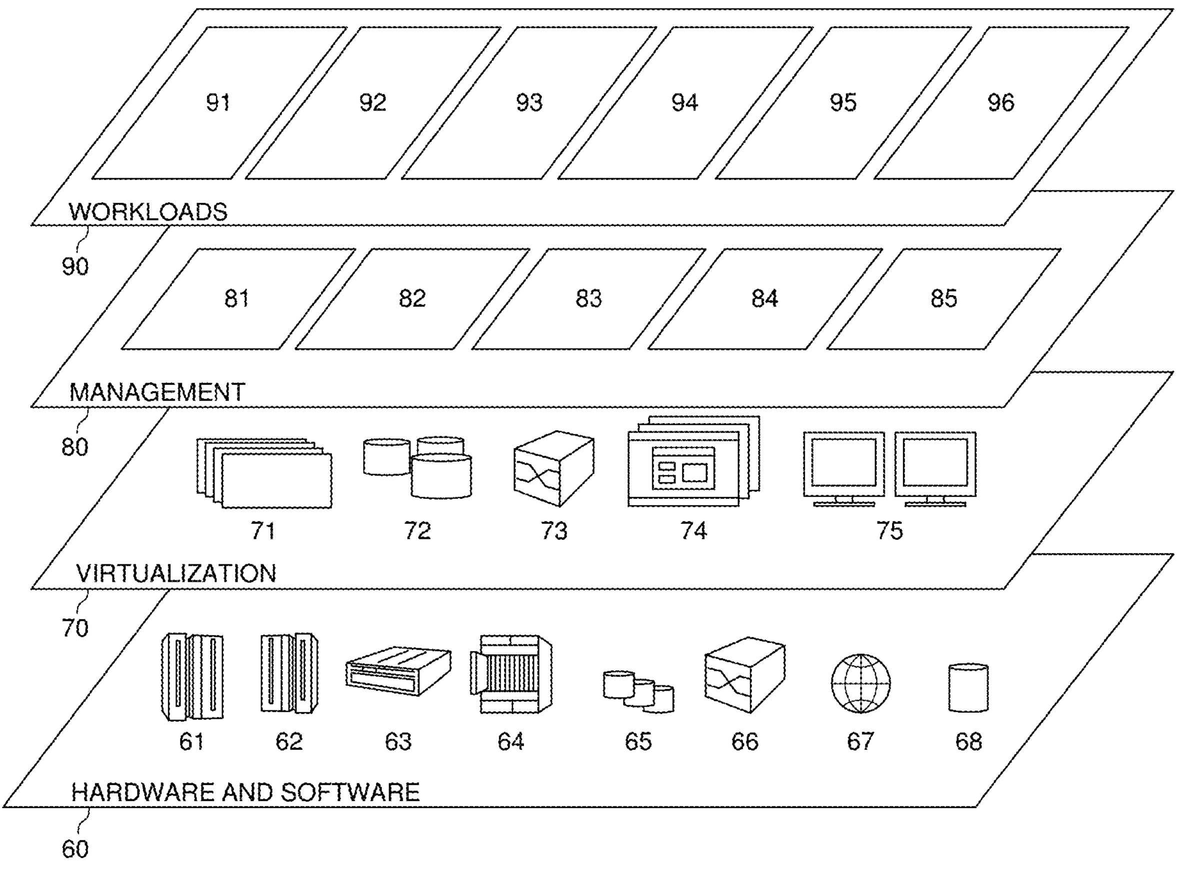
FIG. 6 is a block diagram of functional layers of the illustrative cloud computing environment of FIG. 5, according to an embodiment of the present disclosure.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and system for monitoring eye health 96.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While steps of the disclosed method and components of the disclosed systems and environments have been sequentially or serially identified using numbers and letters, such numbering or lettering is not an indication that such steps must be performed in the order recited, and is merely provided to facilitate clear referencing of the method's steps. Furthermore, steps of the method may be performed in parallel to perform their described functionality.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for analyzing data received from smart contact lenses, comprising:

receiving, by a mobile device, biometric data from one or more sensors located on a contact lens substrate on an eye of a user, the biometric data comprising, at least in part, a moisture level of the eye of the user, and wherein the contact lens substrate further comprises a tear fluid storage chamber;

collecting tear fluid in the tear fluid storage chamber, using an osmosis mechanism, during normal secretion and blinking;

identifying a plurality of environmental parameters associated with a location of the user using a plurality of internet-of-things (IoT) devices communicatively connected with the mobile device and the contact lens substrate;

determining the moisture level in the eye of the user, based on the received biometric data from the one or more sensors located on the contact lens substrate on the eye of the user;

comparing the moisture level in the eye of the user to a predetermined threshold based on moisture level patterns of the eye of the user;

in response to determining that the moisture level in the eye of the user is below the predetermined threshold, automatically adjusting at least one of the plurality of environmental parameters associated with the location of the user; and releasing the collected tear fluid from the tear fluid storage chamber, using the osmosis mechanism, to temporarily relieve dry eye symptoms.

2. The method of claim 1, wherein the plurality of environmental parameters comprises at least one of a room temperature, a humidity level, a light intensity in a current location of the user, and air flow direction.

3. The method of claim 1, further comprising:

in response to determining that the eye moisture level is below the predetermined threshold, displaying, by the mobile device, a guide for the user to adjust at least one of an orientation angle of a screen display, a way of holding the screen display, and an eye level using an augmented reality system.

4. The method of claim 1, wherein the biometric data further comprises information regarding at least one of a position of the contact lens substrate within the eye of the user, a movement pattern, a blinking pattern, and a tear evaporation rate.

5. A computer system for analyzing data received from smart contact lenses, comprising:

one or more processors, one or more computer-readable memories, one or more computer-readable tangible storage devices, and program instructions stored on at least one of the one or more storage devices for execution by at least one of the one or more processors via at least one of the one or more memories, wherein the computer system performs a method comprising:

receiving, by a mobile device, biometric data from one or more sensors located on a contact lens substrate on an eye of a user, the biometric data comprising, at least in part, a moisture level of the eye of the user, and wherein the contact lens substrate further comprises a tear fluid storage chamber;

collecting tear fluid in the tear fluid storage chamber, using an osmosis mechanism, during normal secretion and blinking;

identifying a plurality of environmental parameters associated with a location of the user using a plurality of internet-of-things (IoT) devices communicatively connected with the mobile device and the contact lens substrate;

determining the moisture level in the eye of the user, based on the received biometric data from the one or more sensors located on the contact lens substrate on the eye of the user;

comparing the moisture level in the eye of the user to a predetermined threshold based on moisture level patterns of the eye of the user;

in response to determining that the moisture level in the eye of the user is below the predetermined threshold, automatically adjusting at least one of the plurality of environmental parameters associated with the location of the user; and releasing the collected tear fluid from the tear fluid storage chamber, using the osmosis mechanism, to temporarily relieve dry eye symptoms.

6. The computer system of claim 5, wherein the plurality of environmental parameters comprises at least one of a room temperature, a humidity level, a light intensity in a current location of the user, and air flow direction.

7. The computer system of claim 5, further comprising:

in response to determining that the eye moisture level is below the predetermined threshold, displaying, by the mobile device, a guide for the user to adjust at least one of an orientation angle of a screen display, a way of holding the screen display, and an eye level using an augmented reality system.

8. The computer system of claim 5, wherein the biometric data further comprises information regarding at least one of a position of the contact lens substrate within the eye of the user, a movement pattern, a blinking pattern, and a tear evaporation rate.

9. A computer program product, comprising:

one or more computer readable storage media, and program instructions collectively stored on the one or more computer readable storage media, the program instructions comprising:

program instructions to receive, by a mobile device, biometric data from one or more sensors located on a contact lens substrate on an eye of a user, the biometric data comprising, at least in part, a moisture level of the eye of the user, and wherein the contact lens substrate further comprises a tear fluid storage chamber;

program instructions to collect tear fluid in the tear fluid storage chamber, using an osmosis mechanism, during normal secretion and blinking;

program instructions to identify a plurality of environmental parameters associated with a location of the user using a plurality of internet-of-things (IoT) devices, communicatively connected with the mobile device and the contact lens substrate;

program instructions to determine the moisture level in the eye of the user, based on the received biometric data from the one or more sensors located on the contact lens substrate on the eye of the user;

program instructions to compare the moisture level in the eye of the user to a predetermined threshold based on moisture level patterns of the eye of the user;

in response to determining that the moisture level in the eye of the user is below the predetermined threshold, program instructions to automatically adjust at least one of the plurality of environmental parameters associated with the location of the user; and program instructions to release the collected tear fluid from the tear fluid storage chamber, using the osmosis mechanism, to temporarily relieve dry eye symptoms.

10. The computer program product of claim 9, further comprising:

in response to determining that the moisture level in the eye of the user is below the predetermined threshold:

program instructions to display, by the mobile device, a guide for the user to adjust at least one of an orientation angle of a screen display, a way of holding the screen display, and an eye level using an augmented reality system.

11. The computer program product of claim 9, wherein the plurality of environmental parameters comprises at least one of a room temperature, a humidity level, a light intensity in a current location of the user, and air flow direction.

12. The computer program product of claim 9, wherein the biometric data further comprises information regarding at least one of a position of the contact lens substrate within the eye of the user, a movement pattern, a blinking pattern, and a tear evaporation rate.

13. The method of claim 1, further comprising:

providing real-time feedback to the user via an augmented reality system to avoid dry eye symptoms.

14. The method of claim 1, further comprising:

generating a knowledge base of user-specific eye health conditions and associated environmental factors based on collected historical data of the user, wherein the knowledge base identifies user-specific situations in which dry eye symptoms of the user are initiated or aggravated beyond a predetermined threshold.

15. The method of claim 1, further comprising:

generating a recommendation for preventing dry eye symptoms.

* * * * *